United States Patent [19]
Buzzolini et al.

[11] 3,932,481
[45] Jan. 13, 1976

[54] SULFURIC ACID ESTERS OF BIS-(4-HYDROXYPHENYL)-METHANE

[75] Inventors: Mario G. Buzzolini, Convent Station; Robert E. Manning, Mountain Lakes, both of N.J.

[73] Assignee: Shandoz, Inc., E. Hanover, N.J.

[22] Filed: Apr. 8, 1974

[21] Appl. No.: 459,013

Related U.S. Application Data

[63] Continuation-in-part of Ser. No. 258,787, June 1, 1972, abandoned.

[52] U.S. Cl.............. 260/457; 260/613 R; 424/303
[51] Int. Cl.² ................................. C07C 141/18
[58] Field of Search .................................. 260/457

[56] References Cited
UNITED STATES PATENTS 3,237,200  2/1966  Barany et al........................ 260/457
3,528,986  9/1970  Pala..................................... 260/457

FOREIGN PATENTS OR APPLICATIONS 1,315  5/1962  France............................... 260/457

Primary Examiner—James O. Thomas, Jr.
Assistant Examiner—Nicky Chan
Attorney, Agent, or Firm—Gerald D. Sharkin; Robert S. Honor; Thomas O. McGovern

[57]            ABSTRACT

Sulfuric acid esters of bis-(4-hydroxyphenyl)-methane and their pharmaceutically acceptable salts, e.g., sodium bis-(4-hydroxyphenyl)-methane sulfuric acid diester, are useful in the treatment of Lipidemia.

2 Claims, No Drawings

SULFURIC ACID ESTERS OF BIS-(4-HYDROXYPHENYL)-METHANE

This application is a continuation-in-part of copending United States Patent Application Ser. No. 258,787, filed June 1, 1972 now abandoned.

This invention relates to derivatives of bis-(4-hydroxyphenyl)-methane. In particular it relates to sulfuric acid mono and diesters of bis-(4-hydroxyphenyl)methane, methods for preparing the esters, and their use in pharmaceutical compositions.

The compounds of this invention may be represented by the following formula:

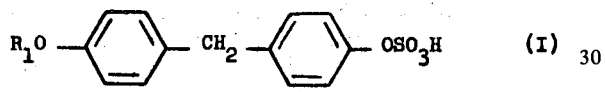 (I)

where
  $R_1$ is hydrogen, benzyl or $SO_3H$ and salts thereof with pharmaceutically acceptable bases.

The preferred compounds are the compounds and salts in which $R_1$ is $SO_3H$, and especially preferred is the sodium salt of bis-(4-hydroxyphenyl)-methane sulfuric acid diester.

The compounds of formula (I) in which $R_1$ is benzyl or $SO_3H$ may be prepared in accordance with the following reaction scheme:

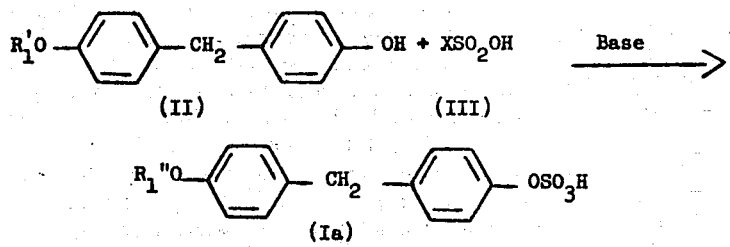

where
  X is halo having an atomic weight of about 35 to 80,
  $R'_1$ is hydrogen or benzyl and
  $R''_1$ is benzyl or $SO_3H$
provided that when $R'_1$ is benzyl, $R''_1$ is also benzyl and when $R_1'$ is hydrogen $R_1''$ is $SO_3H$.

The compound of formula (Ia) are prepared by treating a compound of formula (II) with a halosulfonic acid of formula (III) in the presence of a base at a temperature of from about −50° to about 30°C. The base used in the reaction can be an inorganic base such as sodium hydroxide or sodium bicarbonate or preferably a tertiary amine such as pyridine, triethylamine, diethylaniline and the like. Although a solvent is not necessary, it is preferred that the reaction be run in excess amine or in an inert solvent such a hydrocarbons, e.g., hexane, benzene, toluene and the like, dimethylformamide, dimethylacetamide and especially carbon disulfide. The preferred temperature range is −10°C to +10°C. The time of the reaction is not critical, but is is normally run for about 30 minutes to 2 hours for optimum results. Halide ion formed during the reaction may be removed by standard techniques, e.g., treatment with barium hydroxide. The product (Ia) is recovered by conventional techniques, e.g., evaporation and recrystallization.

The compounds of formula (I) in which $R_1$ is hydrogen may be prepared in accordance with the following reaction scheme:

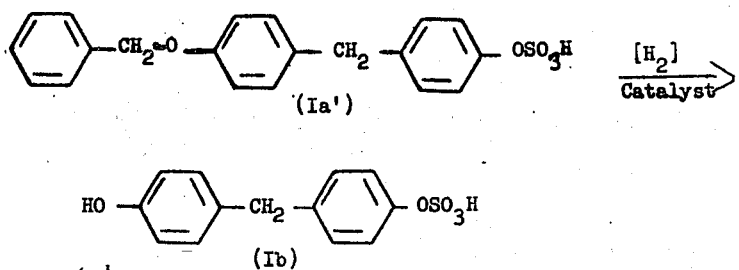

The compounds of formula (Ib) may be prepared by hydrogenating the compound of formula (Ia') or a soluble salt thereof in the presence of a hydrogenation catalyst in an inert solvent. The preferred salt forms are the alkali metal salts, preferably sodium. The hydrogenation catalyst is preferably a platinum or palladium catalyst especially 10% platinum or palladium on carbon. The inert solvents preferred are water; esters such as ethyl acetate; the lower alcohols, especially methanol, ethanol, or isopropyl alcohol; and ethers, such as dioxane and tetrahydrofuran or mixtures thereof. The temperature of the reaction and the pressure of the hydrogen are not critical in the hydrogenation. The process can be carried out at a temperature of about 0° to 50°C., preferably 20° to 30°C., especially between 20° and 25°C. The hydrogenation is carried out preferably at pressure which vary from about 14 psi (about 1 atmosphere) to about 50 psi. Compound (Ib) is recovered by conventional techniques, e.g., by evaporation and recrystallization.

The compounds of formula (I) form pharmaceutically acceptable salts with such cations as sodium, potassium, calcium, magnesium and the like and such salts are included within the scope of the present invention. The salts are prepared by conventional techniques e.g., by dissolving the ester in a suitable solvent, e.g., water or lower alkanol such as methanol, ethanol and the like or in a mixture of water and lower alkanol and treating the ester with an oxide or hydroxide of the desired cation. Conversely the salts are converted back to the esters by treatment with an acid e.g., sulfuric acid, hydrochloric acid, and the like in a similar solvent. The compounds of formula (I) and their salts also form hydrates, which are included within the scope of the present invention.

The compounds of formula (II) in which $R_1'$ is benzyl are novel and may be prepared by the following reaction scheme:

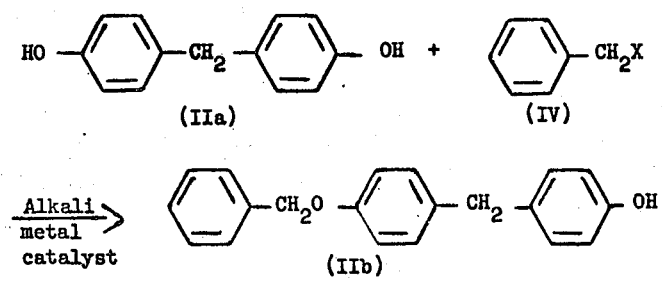

where X is as defined above.

The compounds of formula (IIb) can be prepared by treating a compound of formula (IIa) with a compound of formula (IV) in the presence of an alkali metal such as sodium, potassium, and the like; alkali metal hydrides, such as sodium hydride, potassium hydride and the like; or an alkali metal salt such as potassium carbonate, preferably sodium or sodium hydride. Although a solvent is not required, it is preferred that the reaction be run in an inert solvent, e.g. dimethylformamide, dimethylacetamide, ethers such as tetrahydrofuran and the like, or acetone when the alkali metal catalyst is an alkali metal carbonate. The temperature is not critical, but is is preferred that the reaction be run at between about 20° to about 150°C, preferably at room temperature when an alkali metal or an alkali metal hydride is used as the catalyst or at the reflux temperature of the reaction medium, when an alkali metal carbonate is used as the catalyst. The time of the reaction also is not critical, but it is preferred that the reaction be run for at least 30 minutes. Because the above reaction also yields the dibenzyl ether, the monobenzyl ether (II) must be separated from it. This can be done by standard techniques, for example, crystallization and column chromatography.

The compounds of formula (IIa), (III) and (IV) are known and may be prepared by techniques which are disclosed in the literature.

The compounds of the formula (I) are useful because they possess pharmacological activity in animals. In particular, the compounds of formula (I) are useful as hypolipidemic agents as indicated by the fall in cholesterol and triglyceride levels in male albino Wistar rats weighing 110–130 g initially. The rats are maintained on drug-free laboratory chow diet for seven days and then divided into groups of 8 to 10 animals. Each group, with the exception of the control, is then given orally 7.5, 30, 250 and 500 milligrams per kilogram of body weight per diem of the compound for six days. At the end of this period, the animals are anesthetized with sodium hexobarbital and bled from the carotid arteries. Serum or plasma samples are collected and 1.0 ml of the serum is added to 9.0 ml redistilled isopropanol. Two autoanalyzer cupsful of a mixture of zeolite-copper hydroxide and Lloydds reagent (Kersler, G., and Lederer, H., 1965, Technicon Symposium, Madiad Inc., New York, 345–347) are added, and the mixture is shaken for 1 hour. Cholesterol and triglyceride are determined simultaneously on the same sample by Technicon N 24A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usages, compounds (I) or their pharmaceutically acceptable salts may be administered orally or parenterally as such or admixed with conventional pharmaceutical carriers or adjuvants. They may be administered orally in such forms as tablets, dispersible powders, granules, capsules, syrups, elixirs, suspensions and the like or parenterally as injectable solutions, suspensions, dispersions, emulsions, and the like. These pharmaceutical preparations may contain up to about 90% of the active ingredient in combination with the carrier or adjuvant.

The lipidemia effective dosage of active ingredient employed for the treatment of lipidemia may vary depending on the particular compound employed, the mode of administration and the severity of the condition being treated. However, in general, satisfactory results are obtained when the compounds (I) are administered at a daily dosage of from about 2 milligrams to about 500 milligrams per kilogram of animal body weight, preferably given in divided doses two to four times a day, or in sustained release form. For most large mammals, the total daily dosage is from about 150 to about 3000 milligrams. Dosage forms suitable for internal use comprise from about 37.5 to about 1500 milligrams of the active compounds in intimate admixture with a solid or liquid pharmaceutically acceptable carrier or diluent.

The preferred pharmaceutical compositions from the standpoint of preparation and ease of administration are solid compositions, particularly hard-filled capsules and tablets containing from about 200 to 500 milligrams of the active ingredient.

The representative formulation suitable for oral administration is a capsule prepared by standard encapsulating techniques which contains the following and may be administered 2 to 4 times a day in the treatment of lipidemia:

| Ingredients | Weight (mg) |
| --- | --- |
| sodium bis-(4-hydroxyphenyl)-methane sulfuric acid diester | 200 |
| Inert filler (lactose. kaolin, starch) | 200 |

EXAMPLE 1

Sodium bis-(4-hydroxyphenyl)methane sulfuric acid diester

A solution of 37.5 g. of diethylaniline in 30 ml of carbon disulfide is stirred mechanically and cooled to −10°C. To the solution, 12.5 g of chlorosulfonic acid is added dropwise while the temperature is maintained below 10°C. Ten grams of bis-(4-hydroxyphenyl)methane in 35 ml of carbon disulfide is then added. The mixture is stirred for an hour at room temperature and then poured with stirring into a solution of 8.25 g. of sodium hydroxide and 3.75 g. of hydrated barium hydroxide in 300 ml of water. After extraction with benzene the aqueous phase is evaporated yielding the product, sodium bis-(4-hydroxyphenyl)methane sulfuric acid diester which is recrystallized from ethanol/water. (m.p.>210°C with decomposition).

The sodium bis-(4-hydroxyphenyl)methane sulfuric acid diester of this example is an effective hypolipidemic agent when orally administered to an animal suffering from lipidemia at a dosage of 200 milligrams twice a day.

EXAMPLE 2

Sodium-α-(p-benzyloxyphenyl)-p-cresol sulfate

Step A: α-(p-benzyloxyphenyl)-p-cresol

To a stirred suspension of 3.36 g of sodium hydride (in mineral oil) in 50 ml of dimethylformamide is added dropwise at room temperature a solution of 15 g bis-(p-hydroxyphenyl)-methane in 50 ml dimethylformamide. The resulting solution is stirred at room temperature for one hour. Ten grams of benzyl chloride is added dropwise and the stirring is continued at room temperature overnight. After evaporation of the solvent under reduced pressure, the residue is treated with 100 ml of water and extracted twice with diethyl ether. The combined ether extracts are combined, dried over anhydrous magnesium sulfate, evaporated to dryness, and the resulting oil dissolved in hot ethanol. Bis-p-(benzyloxy)phenyl-methane (m.p. 109.5°–110°C) crystallizes upon cooling and is collected by filtration. The mother liquors are evaporated to dryness and the crystalline mono-addition product is obtained by chromatography on silica gel with chloroform. After separation, the mono-benzyl ether is recrystallized from isopropyl ether, m.p. 95°–96°C.

Step B: Sodium-α-(p-benzyloxyphenyl)-p-cresol sulfate

A solution of 21.0 g. of diethylaniline in 7 ml. of carbon disulfide is stirred mechnically and cooled to −10°C. To the solution 8.2 g. of chlorosulfonic acid is added dropwise, while the temperature is maintained below 10°C. Twenty g of α-(p-benzyloxyphenyl)-p-cresol in 7 ml carbon disulfide is then added, and the mixture stirred for an hour. The disulfide is removed by distillation under reduced pressure, and the residue is added to a solution of sodium hydroxide (11.2 g) and hydrated barium hydroxide (3.0 g) in 300 ml water with vigorous shaking. The white precipitate which forms is collected by filtration and the product, sodium -α-(p-benzyloxyphenyl)-p-cresol sulfate is recrystallized twice from ethanol (m.p. > 220°C with decomposition).

EXAMPLE 3

Sodium bis-(4-hydroxyphenyl)methane monosulfate ester.

A solution of 9.0 g of the sodium salt of α-(p-benzyloxyphenyl)-p-cresol sulfate in 450 ml methanol and 50 ml ethyl acetate is hydrogenated over 1 g of 10%-palladium on charcoal at atmospheric pressure. The catalyst is then separated by filtration through celite and the solvent evaporated. The white product obtained, sodium bis-(4-hydroxyphenyl)methane monosulfate ester, is recrystallized from isopropanol (m.p. >200°C with decomposition.)

What is claimed is:

1. A compound of the formula

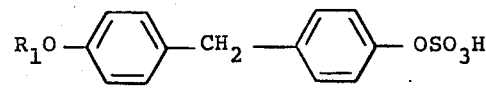

where
   $R_1$ is $SO_3H$, or salts of said compound with pharmaceutically acceptable bases.

2. The compound of claim 1 which is sodium bis-(4-hydroxyphenyl) methane sulfuric acid diester.

* * * * *